(12) United States Patent  
Rajagopal et al.

(10) Patent No.: US 9,243,277 B2  
(45) Date of Patent: Jan. 26, 2016

(54) SENSOR PROBE FOR BIO-SENSING AND CHEMICAL-SENSING APPLICATIONS

(71) Applicant: CALIFORNIA INSTITUTE OF TECHNOLOGY, Pasadena, CA (US)

(72) Inventors: Aditya Rajagopal, Irvine, CA (US); Axel Scherer, Barnard, VT (US); Michael D. Henry, Altadena, CA (US); Sameer Walavalkar, Studio City, CA (US); Thomas A. Tombrello, Altadena, CA (US); Andrew P. Homyk, South Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 14/753,741

(22) Filed: Jun. 29, 2015

(65) Prior Publication Data

US 2015/0299757 A1  Oct. 22, 2015

Related U.S. Application Data

(62) Division of application No. 13/852,476, filed on Mar. 28, 2013, now Pat. No. 9,099,436.

(60) Provisional application No. 61/617,528, filed on Mar. 29, 2012.

(51) Int. Cl.  
*G01R 1/067* (2006.01)  
*G01R 31/00* (2006.01)  
(Continued)

(52) U.S. Cl.  
CPC .............. *C12Q 1/02* (2013.01); *A61B 5/04001* (2013.01); *G01N 27/3275* (2013.01);  
(Continued)

(58) Field of Classification Search  
CPC ........... G01R 1/07342; G01R 1/06711; G01R 1/06738; G01R 1/06772; G01R 3/00; C12Q 1/02; C12Q 1/6825; C12Q 1/6869; G01N 27/4145; G01N 27/414; G01N 33/5438; G01N 33/5008; G01N 33/5058; G01N 33/5073; A61B 5/04001; A61B 5/0478; A61B 5/103; A61B 2562/0209; A61M 5/00  
USPC .................. 324/149, 755.01; 604/66; 506/10; 435/6.11; 436/518; 600/372, 587; 607/2  
See application file for complete search history.

(56) References Cited

U.S. PATENT DOCUMENTS 5,246,013 A * 9/1993 Frank .................... A61B 5/0051  
600/587  
5,561,479 A * 10/1996 Lee .......................... H04N 5/50  
348/733

(Continued)

FOREIGN PATENT DOCUMENTS

EP  0803702 A2 * 10/1997 ............... G01B 7/34  
EP  2353636 A1 * 8/2011 ......... A61B 5/04001

OTHER PUBLICATIONS

Final Office Action issued on May 8, 2015 for U.S. Appl. No. 14/463,392, filed Aug. 19, 2014 in the name of Aditya Rajagopal.

(Continued)

*Primary Examiner* — Jermele M Hollington  
*Assistant Examiner* — Sean Curtis  
(74) *Attorney, Agent, or Firm* — Steinfl & Bruno LLP (57) ABSTRACT

The basic structure and functionality of a probe as disclosed herein allows for flexibly incorporating into the probe, various sensing elements for various sensing applications. Two example applications among these various sensing applications include bio-sensing and chemical-sensing applications. For bio-sensing applications the probe, which is fabricated upon a silicon substrate, includes a bio-sensing element such as a nano-pillar transistor, and for chemical-sensing applications the probe includes a sensing element that has a functionalized contact area whereby the sensing element generates a voltage when exposed to one or more chemicals of interest.

14 Claims, 5 Drawing Sheets

(51) Int. Cl.
*C12Q 1/02* (2006.01)
*H01L 29/78* (2006.01)
*H01L 29/66* (2006.01)
*G01N 27/327* (2006.01)
*G01N 27/414* (2006.01)
*A61B 5/04* (2006.01)
*H01L 29/41* (2006.01)
*H01L 29/423* (2006.01)
*H01L 29/49* (2006.01)
*G01R 1/073* (2006.01)

(52) U.S. Cl.
CPC ....... *G01N 27/4146* (2013.01); *G01R 1/06711* (2013.01); *H01L 29/413* (2013.01); *H01L 29/42376* (2013.01); *H01L 29/4966* (2013.01); *H01L 29/66477* (2013.01); *H01L 29/78* (2013.01); *H01L 29/7831* (2013.01); *G01R 1/07342* (2013.01)

(56) References Cited

U.S. PATENT DOCUMENTS

| | | | | |
|---|---|---|---|---|
| 5,784,541 | A * | 7/1998 | Ruff | G05B 19/0426 345/473 |
| 6,665,562 | B2 * | 12/2003 | Gluckman | A61N 1/36014 128/898 |
| 7,182,914 | B2 * | 2/2007 | Lai | B82Y 5/00 257/27 |
| 7,462,324 | B2 * | 12/2008 | Ozaki | G01N 33/48707 422/50 |
| 7,622,934 | B2 * | 11/2009 | Hibbs | G01N 33/48728 204/400 |
| 7,659,149 | B2 * | 2/2010 | Yoo | G01N 33/54306 257/256 |
| 7,692,218 | B2 * | 4/2010 | Barron | B82Y 10/00 257/253 |
| 8,017,938 | B2 * | 9/2011 | Gomez | B82Y 15/00 257/40 |
| 8,154,058 | B2 * | 4/2012 | Hwang | G01N 27/4145 257/253 |
| 8,355,768 | B2 * | 1/2013 | Masmanidis | A61B 5/04001 600/372 |
| 2002/0081588 | A1 * | 6/2002 | De Lumley-woodyear | B01J 19/0046 435/6.11 |
| 2005/0003396 | A1 * | 1/2005 | Ozkan | C12Q 1/6825 435/6.11 |
| 2005/0045875 | A1 * | 3/2005 | Lai | B82Y 5/00 257/40 |
| 2006/0188904 | A1 * | 8/2006 | Ozkan | C12Q 1/6825 435/6.11 |
| 2008/0063566 | A1 * | 3/2008 | Matsumoto | G01N 33/5438 422/68.1 |
| 2008/0132422 | A1 * | 6/2008 | Bohlen | G01N 33/5008 506/10 |
| 2009/0177144 | A1 * | 7/2009 | Masmanidis | A61B 5/04001 604/66 |
| 2010/0248284 | A1 * | 9/2010 | Chen | G01N 33/48728 435/29 |
| 2010/0268078 | A1 * | 10/2010 | Scarantino | A61B 5/0031 600/436 |
| 2010/0286686 | A1 * | 11/2010 | Hancock | A61B 18/18 606/33 |
| 2011/0218490 | A1 * | 9/2011 | Ocvirk | A61B 5/14532 604/66 |
| 2011/0248320 | A1 * | 10/2011 | Rothberg | G01N 27/4145 257/253 |
| 2011/0288391 | A1 * | 11/2011 | Rao | A61B 5/04001 600/373 |
| 2013/0167360 | A1 * | 7/2013 | Masmanidis | A61B 5/04001 29/592.1 |

OTHER PUBLICATIONS

Non-Final Office Action for U.S. Appl. No. 14/463,392, filed Aug. 19, 2014 on behalf of Aditya Rajagopal. mailed Aug. 27, 2015.

* cited by examiner

SENSOR PROBE FOR BIO-SENSING AND CHEMICAL-SENSING APPLICATIONS

CROSS REFERENCE TO RELATED APPLICATIONS

The present application is a divisional of U.S. patent application Ser. No. 13/852,476, filed on Mar. 28, 2013, which claims priority under 35 U.S.C. §119(e) from U.S. Provisional Patent Application No. 61/617,528 entitled "Trans-membrane Pillar FET" filed on Mar. 29, 2012, both of which are incorporated herein by reference in their entirety. Furthermore, the present application is related to U.S. patent application Ser. No. 13/852,480 filed on Mar. 28, 2013, entitled "Nano-pillar Transistor Fabrication and Use," and U.S. patent application Ser. No. 14/463,392 filed on Aug. 19, 2014, entitled "Nano-pillar Transistor Fabrication and Use," both of which are also incorporated herein by reference in their entirety.

STATEMENT OF FEDERAL GOVERNMENT SUPPORT

This invention was made with government support under W911NF-07-1-0277 awarded by the Army Research Office. The government has certain rights in the invention.

FIELD

The present teachings generally relate to a probe. In particular, the present teachings relate to a sensor probe for use in bio-sensing and/or chemical-sensing applications.

BACKGROUND

Extracellular probes are often too large for use in applications where the target cells in a cellular membrane, for example, have relatively small sizes. For example, extracellular probes are generally too big for measuring single neuron behavior. Even when miniaturized, many prior art probes suffer from other handicaps such as being vibration sensitive and causing cell death due to materials incompatibility. It is therefore desirable to provide a probe that is not only small in size but is also suitable for performing various types of measurements upon a variety of target objects having different sizes and densities.

SUMMARY

According to a first aspect of the present disclosure, a probe includes a substrate having a major portion configured for placement of one or more processing components, and a first protruding portion extending from the major portion. A first sensor array that is mounted upon a distal end of the first protruding portion includes at least one sensing element having a functionalized contact area that is adapted for detecting at least one of an extracellular field potential or an ionic field potential.

According to a second aspect of the present disclosure, a method includes placing at least a first protruding portion of a probe at a first desired measurement location that provides contact with one of a biological specimen or a chemical specimen; and using a functionalized contact area of a first sensing element mounted on the first protruding portion to sense one of an extracellular field potential or an ionic field potential generated by the one of the biological specimen or the chemical specimen respectively.

Further aspects of the disclosure are shown in the specification, drawings and claims of the present application.

BRIEF DESCRIPTION OF THE DRAWINGS

Many aspects of the present disclosure can be better understood with reference to the following drawings. The components in the drawings are not necessarily drawn to scale. Instead, emphasis is placed upon clearly illustrating various principles. Moreover, in the drawings, like reference numerals designate corresponding parts throughout the several views.

DETAILED DESCRIPTION

Throughout this description, embodiments and variations are described for the purpose of illustrating uses and implementations of the inventive concept. The illustrative description should be understood as presenting examples of the inventive concept, rather than as limiting the scope of the concept as disclosed herein. It will be understood that various labels such as, for example, functionalized contact area, biomimitec and membrane are used herein as a matter of convenience and are to be interpreted appropriately in the context of the description without attaching illogical and unusual restrictions to these terms.

The basic structure and functionality of a probe as disclosed herein allows for flexibly incorporating into the probe, various sensing elements for various sensing applications. Two example applications among these various sensing applications include bio-sensing and chemical-sensing applications. For bio-sensing applications the probe, which is fabricated upon a silicon substrate, includes a bio-sensing element such as a nano-pillar transistor, and for chemical-sensing applications the probe includes a sensing element that has a functionalized contact area whereby the sensing element generates a voltage when exposed to one or more chemicals of interest.

Figure 1:
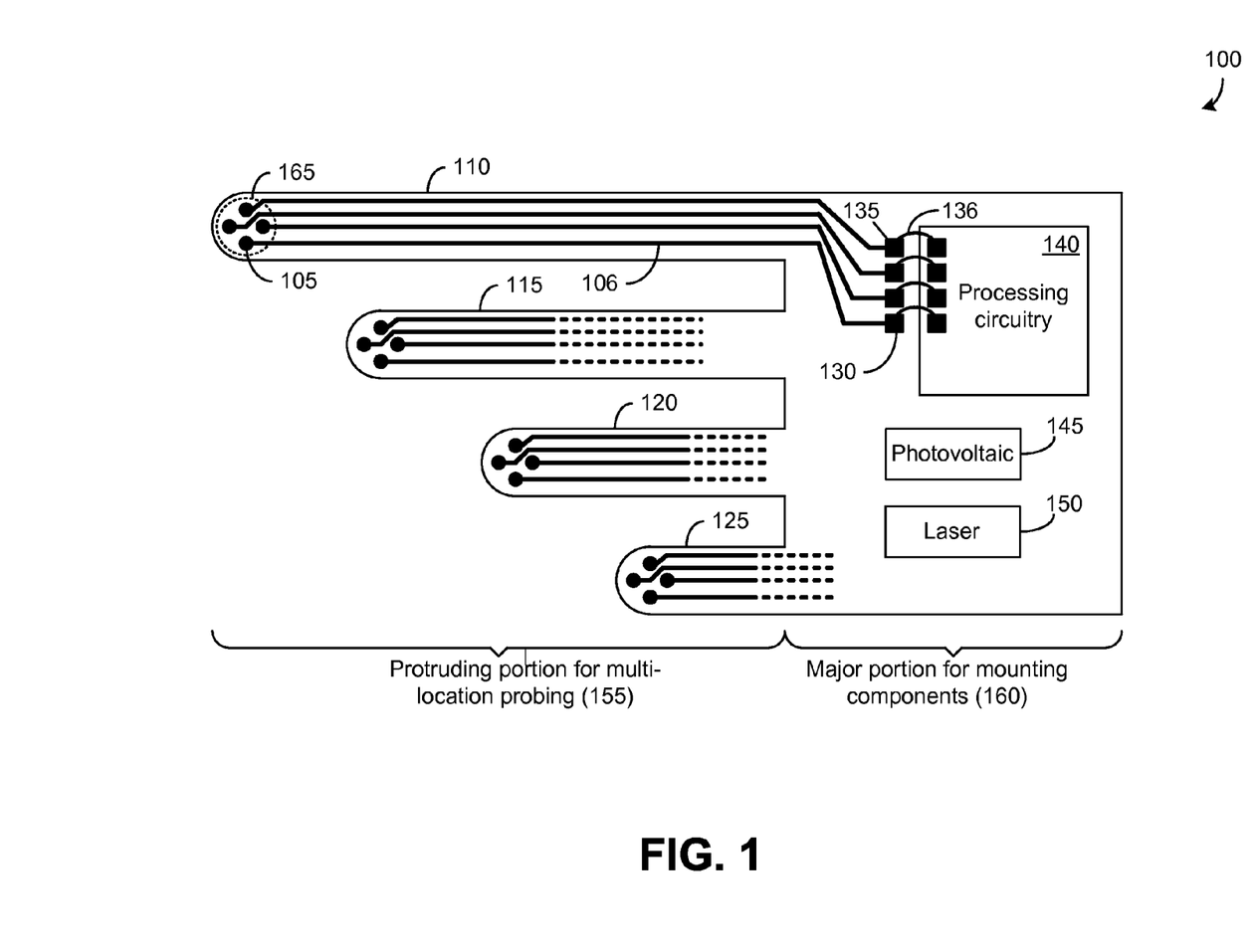
FIG. 1 shows an example embodiment of a probe in accordance with the disclosure.

Attention is first drawn to FIG. 1, which shows an example embodiment of a probe 100 in accordance with the disclosure. Probe 100 is fabricated on a silicon substrate (described below using FIG. 2) and may be broadly partitioned into two portions—a major portion 160 upon which various components may be mounted, and a protruding portion 155 which can include one or more fingers each having a sensor array 165 mounted on a distal end. Four fingers 110, 115, 120 and 125 are included in the example embodiment shown in FIG. 1. In other embodiments, less than, or more than, four fingers may be included.

Sensor array 165 located at a distal end of finger 110 includes two or more sensing elements (this example embodiment shows four sensing elements). The size, number, shape and arrangement of these sensing elements is flexible and is selected, at least in part, based on the nature of the application such as bio-sensing or chemical-sensing of specific substances, for example.

For example, when sensor array 165 is configured for sensing cellular voltage potentials, each of the sensing elements may occupy a maximum area of 10 μm×10 μm based on cell sizes that range from about 1 μm to about 5 μm in diameter. The separation distance between the sensing elements is about 50 μm in this example embodiment.

As a further example, when sensor array 165 is configured for chemical-sensing, each of the sensing elements may occupy a maximum area of 50 nm×50 nm that is based on an ionic concentration.

In the example embodiment shown in FIG. 1, the four fingers 110, 115, 120 and 125 have different protrusion lengths. In other embodiments, two or more fingers may be similar in length, or may have a different protrusion pattern (in contrast to the pattern wherein fingers 110, 115, 120 and 125 are sequentially arranged in a decreasing order based on length).

When different protrusion lengths are employed, the sensor arrays in the various fingers can be used for bio-sensing or chemical-sensing at specific staggered locations. This type of arrangement provides various types of information about a target specimen. For example, the information can be used to determine density values, gradient values, or dispersion values of say, a particular type of ion of interest. Dimensions (such as the height) of one or more of the sensing elements may also be selected for bio-sensing or chemical-sensing at locations corresponding to various heights above a major surface of the substrate of probe 100.

Each of the sensing elements of sensor array 165 is coupled to a respective electrical conductor which runs the length of finger 110. For example, sensing element 105 is coupled to electrical conductor 106, which connects sensing element 105 to a metal pad 135 located on major portion 160. A bonding wire 136 connects metal pad 135 to another metal pad located in processing circuitry 140.

As a result of this arrangement, any field potential that is detected at sensing element 105 (when a target specimen interacts with sensing element 105) is coupled as a sensed voltage to processing circuitry 140, where the voltage may be processed in various ways. The sensing elements in each of the other sensor arrays are also coupled to respective electrical conductors that run the length of each respective finger and are each connected via metal pads and bonding wires (or other connectivity mechanisms) to processing circuitry 140. To avoid clutter and obfuscation, these additional connections from the other electrical conductors are indicated in FIG. 1 by dashed lines.

Processing circuitry 140 includes various electronic devices, such as, for example, amplifiers, oscillators, analog-to-digital converters, and transmitters that are selected on the basis of any specific application amongst a wide variety of applications.

Various additional devices, such as, for example, photovoltaic power source 145 and laser 150, are coupled to processing circuit 140 for powering purposes and for signal transmission purposes. In one example implementation, photovoltaic power source 145 contains a number of photovoltaic cells that are coupled together to provide +/−1 Volt at 150 μA, and laser 150 is a VCSEL operating at a 850 nm wavelength. In this example embodiment, these parameters are based on a maximum allowable energy density inside an animate object.

U.S. patent application Ser. No. 12/860,723 (Publication No. 2011/0044694 A1) titled "Systems and Methods for Optically Powering Transducers and Related Transducers" (filed Aug. 20, 2010) and incorporated herein by reference in its entirety, provides details of an example application that may be wholly or partially applicable to probe 100.

In various embodiments, the sensing elements of sensor array 165 may be unpowered passive sensing elements or powered active sensing elements. The powered sensing elements are connected to processing circuitry 140 through electrical conductors (such as conductor 106) located on the substrate upon which sensor array 165 is mounted.

Figure 2:
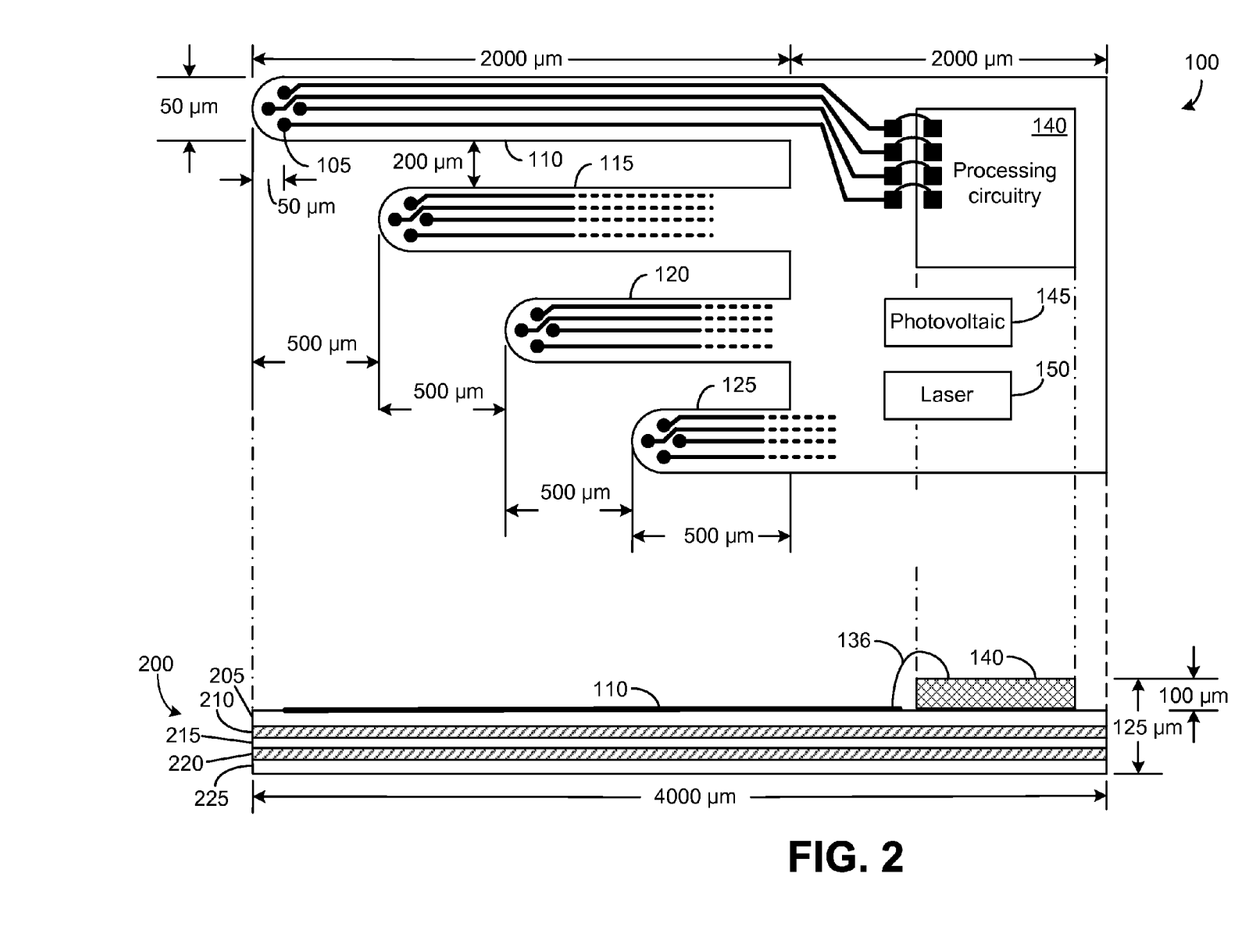
FIG. 2 shows a structural cross-section view of a substrate portion of the probe shown in FIG. 1, along with some example dimensions of various parts of the probe.

Attention is next drawn to FIG. 2, which shows some example dimensions of various parts of probe 100, and also shows a structural cross-section view of a silicon substrate 200 that is a part of probe 100. In the example embodiment shown in FIG. 2, the silicon substrate 200 is a multi-layer substrate that includes two silicon dioxide layers 210 and 220 sandwiched amongst silicon layers 205, 215 and 225.

Figure 3:
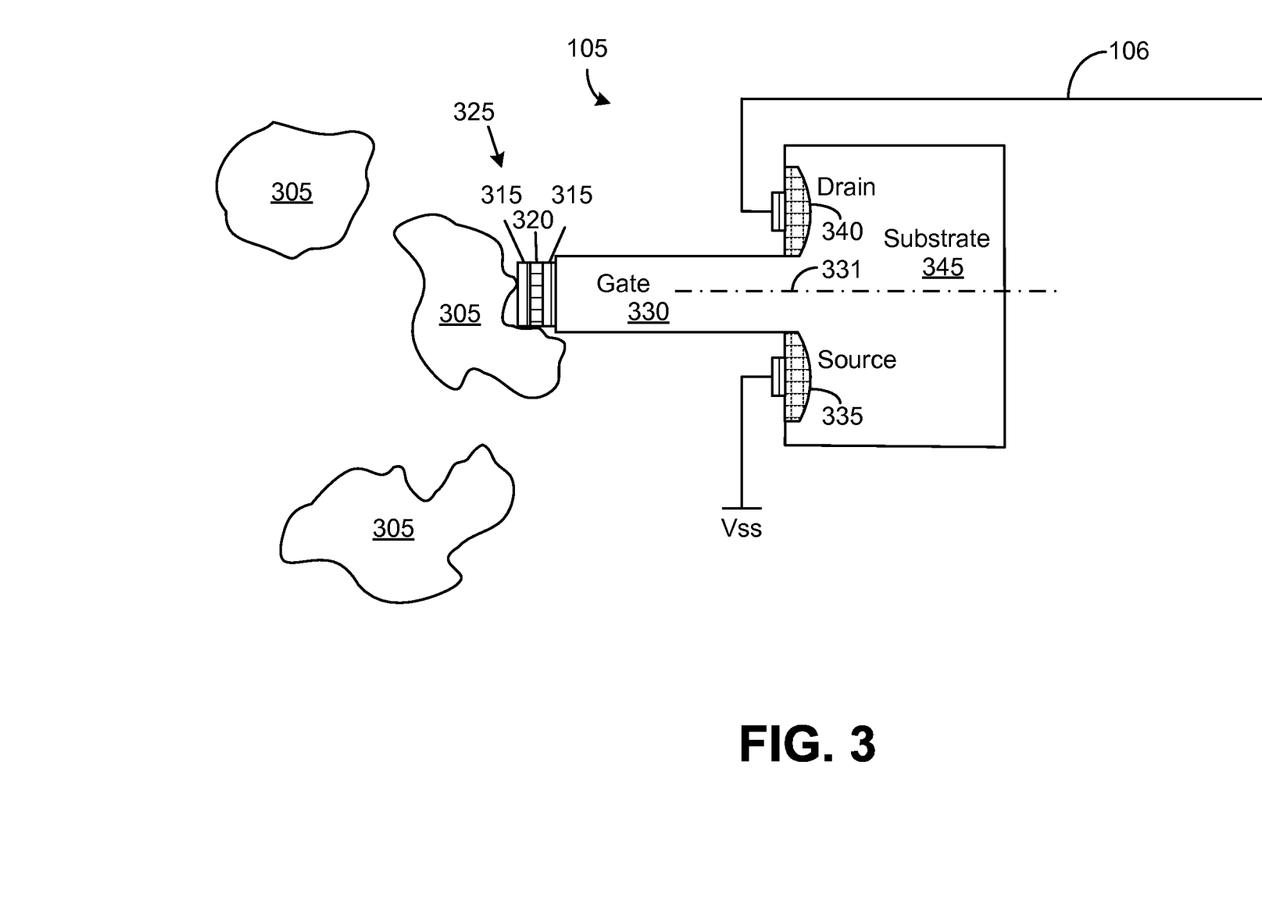
FIG. 3 shows an example first sensing element incorporated into a probe in accordance with the disclosure.

FIG. 3 shows a first example embodiment of a sensing element 105 (shown in FIG. 1 as part of probe 100) in accordance with the disclosure. In this example embodiment, sensing element 105 is a powered sensing element, more particularly, a nano-pillar transistor having a gate 330 that incorporates a biomimitec structure 325.

As is known in the art, field effect transistors can be used as sensors for a variety of applications, including bio-sensing applications. However, in contrast to existing art, a field effect nano-pillar transistor in accordance with the disclosure has a pillar-shaped gate element incorporating a biomimitec portion that provides various advantages over prior art devices. The small size of the nano-pillar transistor disclosed herein allows for advantageous insertion into cellular membranes, and the biomimitec character of the gate element operates as an advantageous interface for sensing small amplitude voltages such as trans-membrane cell potentials. The nano-pillar transistor can be used in various embodiments to stimulate cells, to measure cell response, or to perform a combination of both actions.

In some example embodiments, the nano-pillar transistor disclosed herein can be configured to execute a multiplexed mode of operation (for example, a time-multiplexed mode of operation) whereby the same nano-pillar transistor can be used to inject a current into a cell (writing to the cell) and then measure the electrical response to the current injection (reading the cell).

Further particulars of the nano-pillar transistor are disclosed in U.S. patent application Ser. No. 13/852,480 filed on Mar. 28, 2013, entitled "Nano-pillar Transistor Fabrication and Use," which is incorporated herein by reference in its entirety.

Turning once again to FIG. 3, nano-pillar transistor 105 includes a gate terminal 330 located between source terminal 335 and drain terminal 340. Source terminal 335 is connected to a ground potential, for example, through a ground layer located in the silicon substrate 200 of probe 100. Drain terminal 340 is connected to a power supply voltage, for example, via an electrical conductor such as electrical conductor 106 and a pull-up resistor located in processing circuitry 140.

Gate terminal 330 has a pillar configuration with a linear axis 331 oriented orthogonal to the substrate 345. As shown, gate terminal 330 incorporates a biomimitec structure 325 that mimics certain characteristics of cellular membranes. In one example embodiment, biomimitec structure 325 is a platinum-gold-platinum metal stack formed of a gold layer 320 sandwiched between a pair of platinum layers 315. The platinum-gold-platinum metal stack mimics the hydrophilic-hydrophobic-hydrophilic structure of cellular membranes, allowing for easy integration into biological systems.

A cellular membrane contains numerous cells such as cells 305, which typically vary in shape and size with each other. When gate 330 is selected to have a contact area diameter that roughly corresponds to one cell, a single cell 305 will likely make contact with gate 330. When gate 330 is selected to have a contact area diameter that roughly corresponds to a number of cells, more than one cell 305 will likely make contact with gate 330.

An extracellular field potential generated in or more of cells 305 is (in one example implementation) in the range of −200 mV to 200 mV with respect to solution potential. The extracellular field potential affects a change to gate 330 of nano-pillar transistor 105 resulting in placing nano-pillar transistor 105 in a saturated conduction state. Careful tuning of gate dimensions such as length, width, and geometry can be used to adjust gain, sensitivity, and bandwidth parameters. The voltages associated with the saturated conduction state and a non-conducting condition of nano-pillar transistor 105 can be processed by suitable circuitry located in processing circuitry 140. One example of such processing is provided below using FIG. 5.

Figure 4:
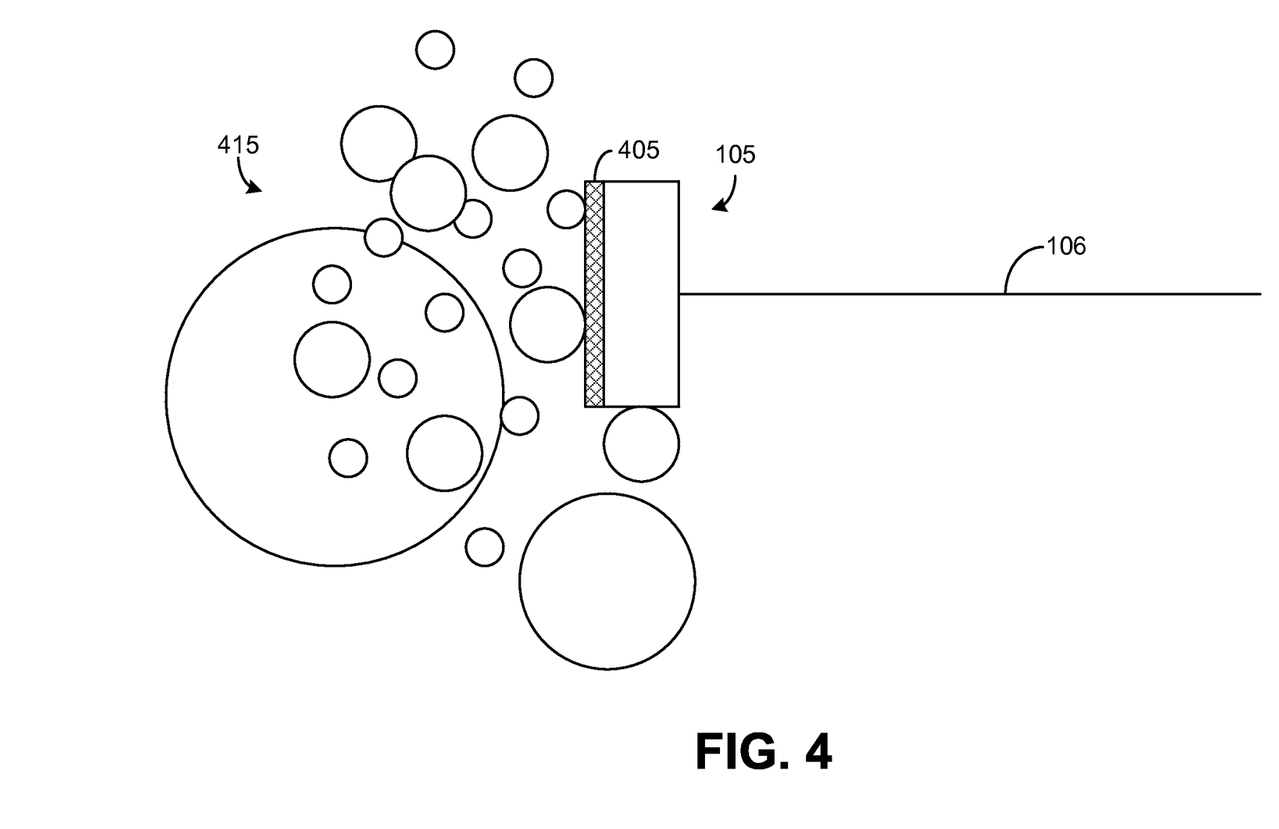
FIG. 4 shows an example second sensing element incorporated into a probe in accordance with the disclosure.

FIG. 4 shows a second example embodiment of a sensing element 105 in accordance with the disclosure. In this example embodiment, sensing element 105 is an unpowered sensing element, more particularly, a chemical sensing element incorporating a functionalized contact area 405. In one example implementation, functionalized contact area 405 includes an n:m ratio of platinum (Pt) and ruthenium (Ru) for sensing methanol. Some example of the n:m ratio is 1:1 and 2:2. In another example implementation, functionalized contact area 405 includes a poly-di-methyl-siloxane surface that can be used to adsorb and sense light metal salts such as Na+, K+, etc.

Each of chemical ions 415 may be similar in size or shape in some applications, and may be different from each other in other applications. In a manner similar to that described above with reference to FIG. 3, when chemical ions 415 come in contact with, or are in proximity to, functionalized contact area 405, an ionic field potential is sensed by sensing element 105 and coupled via electrical conductor 106 to processing circuitry 140.

Figure 5:
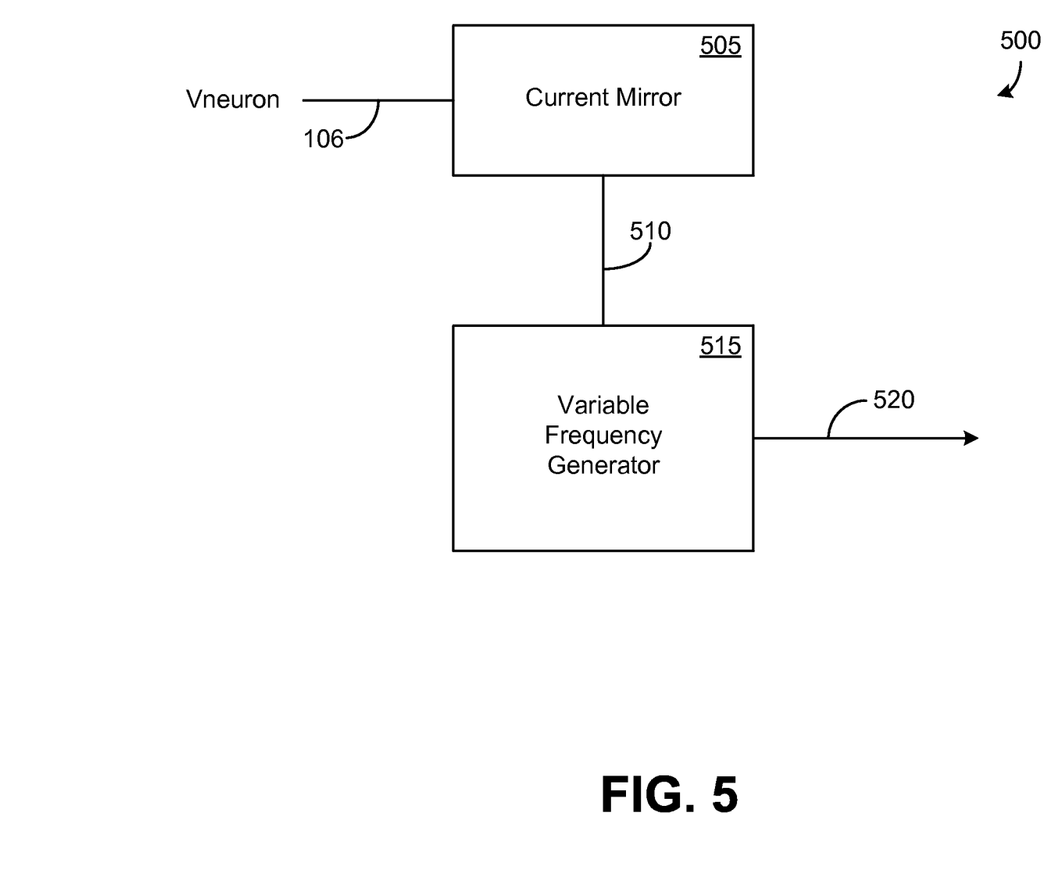
FIG. 5 shows an example processing circuit coupled to a sensing element of a probe in accordance with the disclosure.

FIG. 5 shows one example processing circuit 500, which may be located inside processing circuitry 140 or elsewhere on probe 100. Processing circuit 500 includes a current mirror circuit 500 and a variable frequency generator 515. Current mirror circuit 505 receives a sensed voltage via electrical conductor 106. The sensed voltage corresponds to the on-off conduction state of a nano-pillar transistor (described above using FIG. 3) or generated in functionalized contact area from an ionic field potential (described above using FIG. 4).

The sensed voltage is converted by current mirror circuit 505 into a current that is coupled via line 510 into variable frequency generator 515. In some implementations, variable frequency generator 515 includes a voltage controlled oscillator (not shown).

In one example embodiment, current mirror 505 generates a first control current in response to a first neuron voltage present on line 106. The first control current is propagated via line 510 from current mirror 505 to variable frequency generator 515.

Furthermore, current mirror 505 generates a second control current in response to a second neuron voltage present on line 106. The second control current is also propagated via line 510 from current mirror 505 to variable frequency generator 515.

Variable frequency generator 515 generates a first signal at a first frequency when the first control current is provided via line 510. The first signal is output on line 520. Variable frequency generator 515 generates a second signal at a second frequency when the second control current is provided via line 510. The second signal is also output on line 520. The occurrence of the first and second signals are indicative of different field potentials associated with one or more neurons or a plurality of chemical ions and can be used for carrying out various measurement procedures.

All patents and publications mentioned in the specification may be indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments/implementations of the disclosure have been described. Nevertheless, it will be understood that various modifications may be made without departing from the spirit and scope of the present disclosure. Accordingly, other embodiments are within the scope of the following claims.

What is claimed is:

1. A method comprising:
placing at least a first protruding portion of a probe at a first desired measurement location that provides contact with one of a biological specimen or a chemical specimen; and
using a functionalized contact area of at least one first sensing element mounted on the first protruding portion to sense one of an extracellular field potential or an ionic field potential generated by the one of the biological specimen or the chemical specimen respectively,
wherein the functionalized contact area is defined at least in part by one of a bulk ionic concentration or a size of a cellular specimen,
wherein the first at least one sensing element comprises two or more sensing elements separated from each other by a separation distance that is defined at least in part by the size of the cellular specimen, and
wherein the size of the cellular specimen ranges from about 1 μm to about 5 μm in diameter.

2. The method of claim 1, wherein the probe includes a substrate having a sandwich structure comprising one or more layers of silicon dioxide, and wherein the at least one first sensing element is configured for detecting an ionic field potential generated as part of a chemical reaction in the chemical specimen.

3. The method of claim 2, wherein the at least one first sensing element is an unpowered sensor array.

4. The method of claim 1, wherein the at least one first sensing element includes a biomimetic contact area incorporating at least one metal that mimics at least a portion of a cellular membrane.

5. The method of claim 4, wherein the at least one metal comprises a platinum-gold-platinum combination that mimics a hydrophilic-hydrophobic-hydrophilic structure of the at least a portion of the cellular membrane.

6. The method of claim 4, wherein the at least one first sensing element comprising the biomimetic contact area is an unpowered passive element.

7. The method of claim 1, wherein the at least one first sensing element is a powered active element.

8. The method of claim 7, wherein the powered active element is a nano-transistor.

9. The method of claim 8, wherein the nano-transistor is a nano-pillar transistor that includes a biomimetic gate configured as a pillar structure incorporating a platinum-gold-platinum metal structure that mimics a hydrophilic-hydrophobic-hydrophilic structure of at least a portion of a cellular membrane.

10. The method of claim 1, wherein the probe includes a second protruding portion having a second at least one sensing element, and further comprises:
 placing the second protruding portion of the probe at a second desired measurement location that provides contact with the one of the biological specimen or the chemical specimen; and
 using a functionalized contact area of the second at least one sensing element of the second protruding portion to sense one of another extracellular field potential or another ionic field potential generated by the one of the biological specimen or the chemical specimen respectively.

11. The probe of claim 10, wherein the first protruding portion extends a first length from a major portion of a substrate, and the second protruding portion extends a second length from the major portion of the substrate.

12. The probe of claim 11, wherein the second length is different than the first length.

13. The probe of claim 12, wherein the difference between the second length and the first length is defined at least in part by a distance between a first desired measurement location and a second desired measuring location.

14. The probe of claim 13, wherein a height of the at least one sensing element is defined at least in part by a third desired measuring location.

* * * * *